(12) United States Patent
Mutti et al.

(10) Patent No.: US 7,687,493 B2
(45) Date of Patent: Mar. 30, 2010

(54) PRODUCT, METHOD AND INTERMEDIATES FOR THE PREPARATION OF AZETIDINE DERIVATIVES

(75) Inventors: Stephane Mutti, Le Perreux sur Marne (FR); Michel Lavigne, Chilly Mazarin (FR); Luc Grondard, Mondeville (FR); Joel Malpart, Olivet (FR); Joerg Rieke-Zapp, Frankfurt (DE); Veronique Crocq-Stuerga, Dijon (FR)

(73) Assignee: Aventis Pharma SA, Antony (FR)

( * ) Notice: Subject to any disclaimer, the term of this patent is extended or adjusted under 35 U.S.C. 154(b) by 0 days.

(21) Appl. No.: 11/689,588

(22) Filed: Mar. 22, 2007

(65) Prior Publication Data

US 2007/0270463 A1    Nov. 22, 2007

Related U.S. Application Data

(63) Continuation of application No. PCT/FR2005/002490, filed on Oct. 10, 2005.

(30) Foreign Application Priority Data

Oct. 14, 2004    (FR) .................................. 04 10844

(51) Int. Cl.
*A61K 31/00* (2006.01)

(52) U.S. Cl. .............. 514/210.21; 514/183; 514/210.01
(58) Field of Classification Search ................ 546/171; 514/183
See application file for complete search history.

(56) References Cited

U.S. PATENT DOCUMENTS

| 4,960,832 | A  | * | 10/1990 | Arnold et al. ............. 525/328.8 |
| 5,530,134 | A  | * | 6/1996 | Daneshtalab et al. ........ 546/249 |
| 6,355,631 | B1 | * | 3/2002 | Achard et al. .......... 514/210.21 |
| 2004/0106655 | A1 | * | 6/2004 | Kitajima et al. ............. 514/365 |
| 2007/0167425 | A1 | * | 7/2007 | Nakade et al. ......... 514/210.17 |

OTHER PUBLICATIONS

Rew et al, Solid-Phase Synthesis of Amine-Bridged Cyclic Enkaphalin Analogues via On-Resin Cyclization Utilizing the Fukuyama-Mitsunobu Reaction, 2002, J. Org. Chem., vol. 67, pp. 8820-8826.*

* cited by examiner

*Primary Examiner*—James D Anderson
*Assistant Examiner*—Meghan Finn
(74) *Attorney, Agent, or Firm*—Balaram Gupta

(57) ABSTRACT

The present invention relates to a novel method for the preparation of azetidine derivatives such as N-{1-[bis(4-chlorophenyl)methyl]azetidin-3-yl}-N-quinol-6-ylmethylsulfonamide and the dihydrochloride thereof and N-{1-[bis(4-chlorophenyl)methyl]azetidin-3-yl}-N-(3,5-difluorophenyl)methylsulfonamide.

7 Claims, No Drawings

PRODUCT, METHOD AND INTERMEDIATES FOR THE PREPARATION OF AZETIDINE DERIVATIVES

CROSS REFERENCE TO RELATED APPLICATIONS

This application is a continuation of International application No. PCT/FR2005/002,490, filed Oct. 10, 2005, which is incorporated herein by reference in its entirety; which claims the benefit of priority of French Patent Application No. 04/10,844, filed Oct. 14, 2004.

BACKGROUND OF THE INVENTION

1. Field of the Invention

The present invention relates to a process for preparing azetidine derivatives such as N-{1-[bis(4-chlorophenyl)methyl]azetidin-3-yl}-N-quinol-6-ylmethylsulfonamide and the dihydrochloride thereof, N-{1-[bis(4-chlorophenyl)-methyl]azetidin-3-yl}-N-quinol-6-ylmethylsulfonamide and N-{1-[bis(4-chloro-phenyl)methyl]azetidin-3-yl}-N-(3,5-difluorophenyl)methylsulfonamide.

2. Description of the Art

The product N-{1-[bis(4-chlorophenyl)methyl]azetidin-3-yl}-N-quinol-6-ylmethylsulfonamide in its base form and N-{1-[bis(4-chlorophenyl)methyl]-azetidin-3-yl}-N-(3,5-difluorophenyl)methylsulfonamide are described in patent application WO 01/64634 and is known as having high affinity for cannabinoid receptors and particularly those of CB1 type and is thus useful in the treatment and prevention of disorders affecting the central nervous system, the immune system, the cardiovascular or endocrine system or the respiratory system, and reproductive disorders. Thus, this compound may be used for treating or preventing psychoses, including schizophrenia, anxiety disorders, depression, epilepsy, neurodegeneration, cerebellar and spinocerebellar disorders, cognitive disorders, head injuries, panic attacks, peripheral neuropathy, glaucoma, migraine, Parkinson's disease, Alzheimer's disease, Huntington's chorea, Reynaud's disease, tremor, compulsive-obsessive disorder, senile dementia, thymus disorders, Tourette's syndrome, tardive dyskinesia, bipolar disorders, cancers, drug-induced locomotor disorders, dystonia, endotoxaemic shock, hemorrhagic shock, hypotension, insomnia, immunological diseases, multiple sclerosis, vomiting, asthma, eating disorders (bulimia or anorexia), obesity, memory disorders, in weaning from chronic treatments and alcohol or drug (opioids, barbiturates, cannabis, cocaine, amphetamine, phencyclidine, hallucinogen or benzodiazepines, for example) abuse, as analgesics or as potentiators of the analgesic activity of narcotic and non-narcotic drugs.

SUMMARY OF THE INVENTION

The present invention relates to the development of a process for synthesizing the products N-{1-[bis(4-chlorophenyl)methyl]azetidin-3-yl}-N-quinol-6-ylmethyl-sulfonamide and N-{1-[bis(4-chlorophenyl)methyl]azetidin-3-yl}-N-(3,5-difluoro-phenyl)methylsulfonamide, that is compatible with large-scale production. This production process made it possible to dispense with all the purification steps and all the isolations of intermediates or of the finished product by chromatography on silica, and to use crystallization techniques.

The present invention also relates to the use of N-{1-[bis(4-chlorophenyl)-methyl]azetidin-3-yl}-N-quinol-6-ylmethylsulfonamide dihydrochloride in the treatment and prevention of disorders affecting the central nervous system, the immune system, the cardiovascular or endocrine system or the respiratory system, and reproductive disorders. Thus, this compound may be used for treating or preventing psychoses, including schizophrenia, anxiety disorders, depression, epilepsy, neurodegeneration, cerebellar and spinocerebellar disorders, cognitive disorders, head injuries, panic attacks, peripheral neuropathy, glaucoma, migraine, Parkinson's disease, Alzheimer's disease, Huntington's chorea, Reynaud's disease, tremor, compulsive-obsessive disorder, senile dementia, thymus disorders, Tourette's syndrome, tardive dyskinesia, bipolar disorders, cancers, drug-induced locomotor disorders, dystonia, endotoxaemic shock, hemorrhagic shock, hypotension, insomnia, immunological diseases, multiple sclerosis, vomiting, asthma, eating disorders (bulimia or anorexia), obesity, memory disorders, in weaning from chronic treatments and alcohol or drug (opioids, barbiturates, cannabis, cocaine, amphetamine, phencyclidine, hallucinogen or benzodiazepines, for example) abuse, as analgesics or as potentiators of the analgesic activity of narcotic and non-narcotic drugs in the treatment of metabolic syndrome, visceral obesity and levodopa-induced dyskinesia.

Patent application WO 01/64634 describes a general method for synthesizing N-{1-[bis(4-chlorophenyl)methyl] azetidini-3-yl}-N-(aryl or heteroaryl)methylsulfon-amide, which is incorporated herein by reference in its entirety.

DETAILED DESCRIPTION OF THE INVENTION

The term "aryl" denotes a phenyl, naphthyl or indenyl radical, these aryls being unsubstituted or substituted with one or more halogen, alkyl, alkoxy, formyl, hydroxyl, trifluoromethyl, trifluoromethoxy, —CO-alk, cyano, —COOH, COOalk, amide, alkylsulfanyl, alkylsulfinyl, alkylsulfonyl, alkylsulfanylalkyl, alkylsulfinylalkyl, alkylsulfonylalkyl or hydroxyalkyl. The term "heteroaryl" means benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidyl, quinolyl, 1,2,3,4-tetrahydroisoquinolyl, thiazolyl and thienyl rings, these heteroaryls possibly being unsubstituted or substituted with a halogen, alkyl, alkoxy, hydroxyl, trifluoromethyl, trifluoromethoxy, cyano, —COOH, COOalk, alkylsulfanyl, alkylsulfinyl, alkylsulfonyl, alkylsulfanylalkyl, alkylsulfinylalkyl, alkylsulfonylalkyl or hydroxyalkyl.

Patent application WO 01/64634 describes the synthesis of N-{1-[bis(4-chlorophenyl)methyl]azetidin-3-yl}-N-(aryl or heteroaryl)methyl sulfonamide starting with an intermediate common to N-{1-[bis(4-chlorophenyl)methyl]azetidin-3-yl}-N-(3,5-difluorophenyl)methylsulfonamide and to N-{1-[bis(4-chlorophenyl)methyl]-azetidin-3-yl}-N-quinol-6-ylmethylsulfonamide, namely 1-[bis(4-chlorophenyl)-methyl]azetidin-3-ol and N-(aryl or heteroaryl)methylsulfonamide in the presence of triphenylphosphine and diethyl azodicarboxylate (DEAD) in an inert solvent such as tetrahydrofuran. These products are obtained after one or two chromatographies on silica and/or crystallization.

The present invention relates to an improvement in the process for synthesizing N-{1-[bis(4-chlorophenyl)methyl] azetidin-3-yl}-N-quinol-6-ylmethyl-sulfonamide for scaling up, with isolations allowing high purity of the products without chromatography. The novel synthesis concerning the Mitsunobu reaction, performed in toluene instead of THF, makes it possible to simplify the process by dispensing with the chromatographies on silica, the changes of solvents, the static drying of the organic solutions over dehydrating products (replaced with azeotropic distillations) and makes it possible to crystallize the N-{1-[bis(4-chlorophenyl)-methyl]azetidin-3-yl}-N-(3,5-difluorophenyl)methylsulfonamide and the N-{1-[bis(4-chlorophenyl)methyl]azetidin-3-yl}-N-quinol-6-ylmethylsulfonamide directly from isopropanol without prior column chromatography.

The present invention has also made it possible to obtain a novel product, the novel salt N-{1-[bis(4-chlorophenyl)methyl]azetidin-3-yl}-N-quinol-6-ylmethylsulfonamide dihydrochloride. This salt N-{1-[bis(4-chlorophenyl)methyl]azetidin-3-yl}-N-quinol-6-ylmethylsulfonamide dihydrochloride is obtained in the presence of hydrochloric acid in isopropanol, and preferably in the presence of 5-6N hydrochloric acid in isopropanol.

The production of N-{1-[bis(4-chlorophenyl)methyl]azetidin-3-yl}-N-quinol-6-ylmethylsulfonamide 7 and of N-{1-[bis(4-chlorophenyl)methyl]azetidin-3-yl}-N-(3,5-difluorophenyl)methylsulfonamide 9 is performed according to the synthetic scheme (I):

of sodium borohydride in tetrahydrofuran, and then of acetonitrile in the presence of sulfuric acid.

1,1-Bis(p-chlorophenyl)methylamine is obtained from N-[bis(4-chloro-phenyl)methyl]acetamide 2 in the presence of hydrochloric acid and butanol, and is isolated in the form of the hydrochloride 3.

1-[Bis(4-chlorophenyl)methyl]azetidin-3-ol hydrobromide 4 is prepared from epibromohydrin and [bis(4-chlorophenyl)methyl]amine hydrochloride 3 in the presence of ethanol and sodium bicarbonate, and then in toluene in the presence of hydrobromic acid.

The advantage of using 1-[bis(4-chlorophenyl)methyl]azetidin-3-ol hydrobromide 4 is that it is possible to diversify the chain in position 3 of the azetidine by reacting an N-(aryl or heteroaryl)methylsulfonamide of the type 5 or 8 in the presence of triphenylphosphine and diisopropyl azodicarboxylate (DIAD) in toluene with 1-[bis(4-chlorophenyl)methyl]azetidin-3-ol. It is generally described in WO 01/64634 that the solvent used is refluxing THF with DEAD. It has now

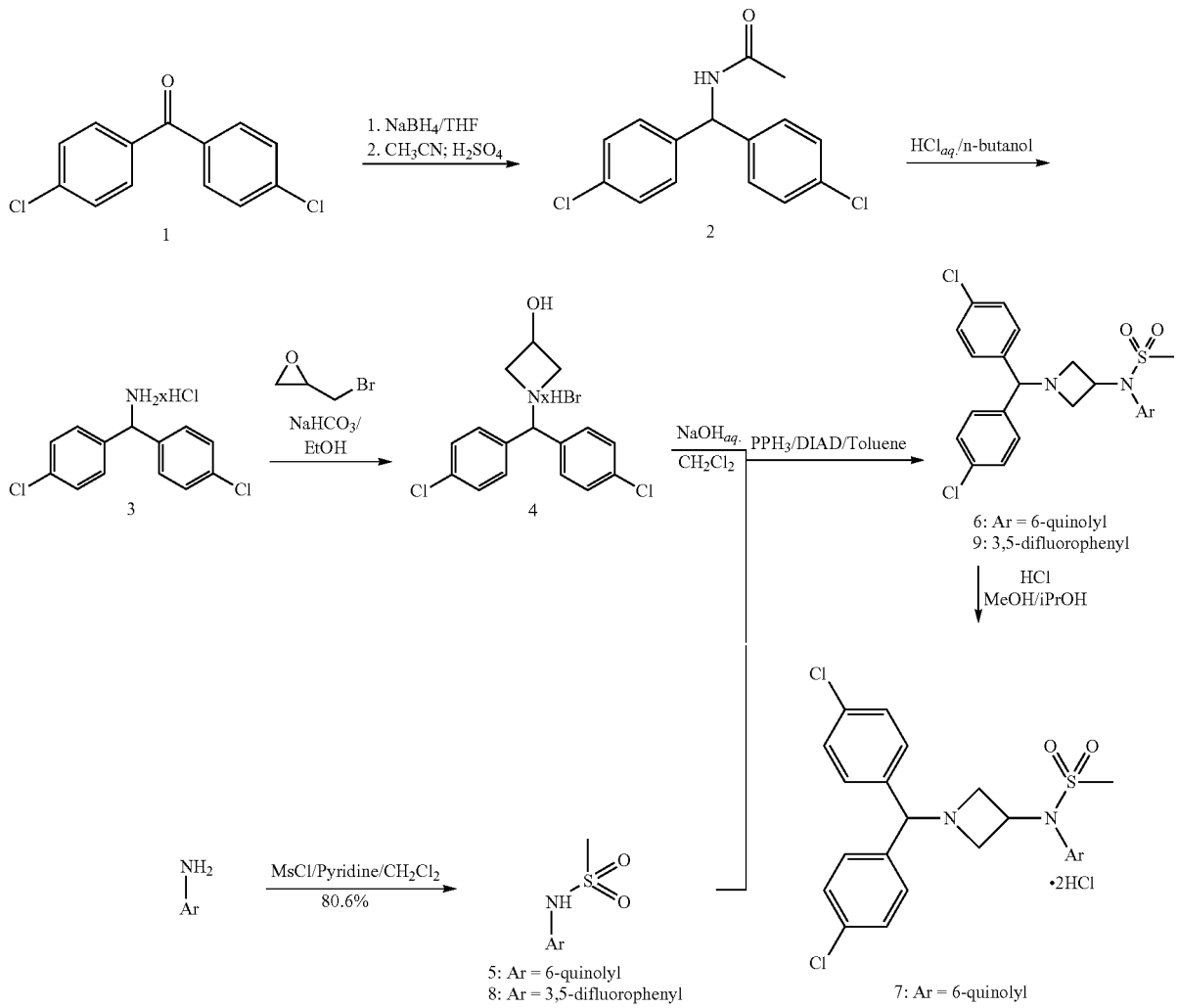

According to the procedure described in synthetic scheme (I), the N-[bis(4-chlorophenyl)methyl]acetamide 2 is obtained from 4,4'-dichlorobenzophenone 1 in the presence been found that toluene is preferable with a temperature of between 40 and 60° C. and preferentially between 50 and 60° C., and makes it possible to dispense with the chromatography step, in particular for N-{1-[bis(4-chlorophenyl)methyl] azetidin-3-yl}-N-quinol-6-ylmethylsulfonamide. When the reaction is complete, a toluene/isopropanol azeotropic distillation makes it possible to remove the toluene, thus leading to crystallization of the N-{1-[bis(4-chlorophenyl)methyl]azetidin-3-yl}-N-quinol-6-ylmethylsulfonamide without causing the triphenylphosphine oxide to precipitate. This improvement thus makes it possible to envisage a large-scale production of such products, which has not been achieved previously with purifications by chromatography.

The present invention has made it possible to provide a process for synthesizing N-{1-[bis(4-chlorophenyl)methyl] azetidin-3-yl}-N-(aryl or heteroaryl)methylsulfonamide, characterized by a) reaction of 1-[bis(4-chlorophenyl)methyl]azetidin-3-ol hydrobromide with N-(aryl or heteroaryl)methanesulfonamide in the presence of DIAD and triphenylphosphine in toluene, to form N-{1-[bis(4-chlorophenyl)methyl]azetidin-3-yl}-N-(aryl or heteroaryl)methylsulfonamide, which is isolated.

The present invention has also made it possible to synthesize N-{1-[bis(4-chlorophenyl)methyl]azetidin-3-yl}-N-quinol-6-ylmethylsulfonamide dihydro-chloride, characterized by a) reaction of 1-[bis(4-chlorophenyl)methyl]azetidin-3-ol hydrobromide with N-quinolin-6-ylmethanesulfonamide in the presence of DIAD and triphenylphosphine in toluene, to form N-{1-[bis(4-chlorophenyl)methyl]azetidin-3-yl}-N-quinol-6-yl-methylsulfonamide (the reaction is preferably performed at a temperature of between 40 and 60° C.), and then b) the N-{1-[bis(4-chlorophenyl)methyl]azetidin-3-yl}-N-quinol-6-ylmethyl-sulfonamide is converted into N-{1-[bis(4-chlorophenyl)methyl]azetidin-3-yl}-N-quinol-6-ylmethylsulfonamide dihydrochloride (preferably in the presence of HCl in isopropanol), which is isolated.

The present invention has also made it possible to synthesize N-{1-[bis(4-chlorophenyl)methyl]azetidin-3-yl}-N-(3,5-difluorophenyl)methanesulfonamide 9, characterized by the reaction of 1-[bis(4-chlorophenyl)methyl]azetidin-3-ol hydrobromide with N-(3,5-difluorophenyl)methanesulfonamide in the presence of DIAD and triphenylphosphine in toluene, to form N-{1-[bis(4-chlorophenyl)methyl]azetidin-3-yl}-N-(3,5-difluorophenyl)methanesulfonamide, which is isolated.

The present invention is illustrated in the synthetic examples that follow:

EXAMPLE 1

Preparation of N-{1-[bis(4-chlorophenyl)methyl] azetidin-3-yl}-N-quinol-6-ylmethyl-sulfonamide and the intermediates thereof according to scheme (I)

Preparation of the intermediate
N-[bis(4-chlorophenyl)methyl]acetamide 0.87 g of sodium borohydride and 40 ml of THF are placed in a 500 ml three-necked flask equipped with a mechanical stirrer, a thermometer, a 25 ml pressure-equalized dropping funnel and a distillation column, and are brought to 65±5° C. 20 g of 4,4'-dichlorobenzophenone dissolved in 120 ml of THF are then added with stirring. 16.5 ml of methanesulfonyl chloride are added to the solution obtained, over a period of 60 minutes. The temperature of the reaction mass is maintained at 65±5° C. for a further one hour. Once the reaction is complete, the reaction mass is cooled to 20±5° C. and 84 ml of 1 molar hydrochloric acid solution are then added. The aqueous phase is removed, the organic phase is then heated to 70±5° C. and about 100 ml of THF are removed by distillation. 120 ml of acetonitrile are added to the reaction mass, precooled to 50±5° C. The temperature of the reaction medium is then brought to 80±5° C. so as to distil off about 100 ml. 15.3 g of 95% sulfuric acid dissolved in 8.5 ml of purified water are then introduced over 30 minutes. The temperature is maintained at 80±5° C. for 3-4 hours. Once the reaction is complete, 300 ml of purified water are added to the reaction mass at 70±5° C., and the resulting mixture is then cooled and maintained at 50±5° C. for 30-40 minutes (until the start of crystallization is observed). The medium is then cooled to 5-10° C. The suspension is then filtered. The cake is then washed with 30 ml of purified water, filtered by suction and dried in an oven under vacuum (40-45° C./5 mmHg) to constant weight.

23.3 g of N-[bis(4-chlorophenyl)methyl]acetamide are thus obtained in a yield of 91.1%.

Preparation of the intermediate
1,1-bis(p-chlorophenyl)methylamine hydrochloride 78.3 g of N-[bis(4-chlorophenyl)methyl]acetamide, 200 ml of n-butanol and 235 ml of purified water are placed in a 2-liter reactor equipped with a mechanical stirrer, a thermometer and a 250 ml pressure-equalized dropping funnel and a condenser, and on which is mounted a bubble counter. 214 ml of 36% hydrochloric acid are then added over 15 minutes via the dropping funnel, at a temperature of 20±5° C. The temperature of the reaction mass is then maintained at 90±5° C. for a period of 10 to 15 hours. Once the reaction is complete, 200 ml of purified water are poured into the reaction mass. The temperature of the medium is then brought to 100±5° C. so as to distil off about 550 ml. A further 200 ml of purified water are added and the distillation is resumed in order to distil off about 100 ml. The reaction medium is then allowed to cool naturally to 20±5° C. over 3-4 hours. The suspension thus obtained is cooled to 5±5° C. and then filtered. The cake is then washed with 80 ml of purified water, filtered by suction and dried in an oven under vacuum (40-45° C./5 mmHg) to constant weight.

74.1 g of 1,1-bis(p-chlorophenyl)methylamine hydrochloride are thus obtained in a yield of 96%.

Preparation of the intermediate
1-[bis(4-chlorophenyl)methyl]azetidin-3-ol
hydrobromide 20 g of 1,1-bis(p-chlorophenyl)methylamine hydrochloride, 120 ml of ethanol and 12.2 g of sodium hydrogen carbonate are placed in a 1-liter reactor equipped with a mechanical stirrer, a thermometer, a 25 ml pressure-equalized dropping funnel and a condenser, and on which is mounted a bubble counter. The reaction mass is then heated at 80±5° C. for a period of one hour, and then cooled to 55±5° C. 16.7 g of epibromohydrin are introduced over 30 minutes via the dropping funnel, and the reaction mass is maintained at a temperature of 55±5° C. for 4-5 hours, and then refluxed for a further 4-5 hours. Once the reaction is complete, the temperature of the medium is lowered to 30±5° C., and 100 ml of toluene and 100 ml of purified water are then introduced. The mixture is stirred for 30 minutes and the aqueous phase is then removed. The organic phase is then washed with twice 50 ml of purified water. 4 ml of aqueous 48 percent hydrobromic acid solution are introduced into the organic phase obtained, and the mixture is stirred for about 30 minutes until the start of crystallization is observed. The suspension is then cooled to 10±5° C., and then filtered. The cake is then washed with 3 times 15 ml of toluene, filtered by suction and dried in an oven under vacuum (50-55° C./10 mmHg) to constant weight.

22.6 g of 1-[bis(4-chlorophenyl)methyl]azetidin-3-ol hydrobromide are thus obtained in a yield of 83.9%.

Preparation of N-quinolin-6-ylmethanesulfonamide 150 g of 6-aminoquinoline, 3000 ml of dichloromethane and then 90.5 g of pyridine are introduced into a 5-liter three-necked round-bottomed flask equipped with a mechanical stirrer, a 250 ml addition funnel and a nitrogen inlet. A clear yellow solution is obtained. The medium is stirred and cooled to 5±2° C.

123.9 g, i.e. 1.06 eq., of methanesulfonyl chloride are added over 30 minutes at 5±2° C.

The medium turns blood red and, at the end of the addition, the temperature of the medium is 12° C.

Ten minutes after the end of the addition, and still at 5±2° C., the reaction medium suddenly thickens (heterogeneous pink reaction medium).

15 minutes after the end of the addition, the cooling bath is removed and the mixture is allowed to warm to room temperature. The medium thickens, and 450 ml of dichloromethane are then added. The medium becomes more stirrable. The reaction mixture is continued to be stirred for about 24 hours at room temperature. The mixture is then cooled to 14±2° C. and 499 ml of tap water are added over 5 minutes. 408 ml of 5N sodium hydroxide are then added over 30 minutes. The addition of sodium hydroxide is slightly exothermic, +4° C.

The pH at the end of the addition of the sodium hydroxide should be 12, and if not, further sodium hydroxide is added to reach this value.

The phases are separated by settling. Two clear yellow phases are obtained. The aqueous phase is washed with 3×300 ml of dichloromethane. The aqueous phase is cooled to 14±2° C. 6N hydrochloric acid is added over 30 minutes. From the addition of the first few ml, a thick yellow precipitation is observed. After continued addition of hydrochloric acid, a red precipitate appeared suddenly. The mixture is stirred at 10° C. for a further 30 minutes and is then left to warm to room temperature. 990 ml of 10% sodium bicarbonate in water are added over 30 minutes at room temperature. At the end of the bicarbonate addition, the pH should be between 8 and 9, and if it is not, an adjustment needs to be made by further addition of sodium bicarbonate solution. A pink colored thick foam is obtained. The mixture is stirred overnight at room temperature and is then cooled to 2±2° C. for one hour, followed by filtration.

The filtrate is rinsed with 3×150 ml of tap water and the pink solid is placed in an oven under vacuum (100 mmbar) at 35° C. to constant weight. 182.8 g of N-quinolin-6-ylmethanesulfonamide are obtained, i.e. a yield of 80.6%.

$^1$H NMR spectrum (300 MHz)—δ in ppm—in DMSO-d6: 3.12 (s, 3H); 7.51 (dd, J=4.5 and 8.5 Hz, 1H); 7.63 (dd, J=2.5 and 9.0 Hz, 1H); 7.75 (d, J=2.5 Hz, 1H); 9.01 (d, J=8.5 Hz, 1H); 8.32 (broad d, J=8.5 Hz, 1H); 8.82 (dd, J=2.0 and 4.5 Hz, 1H); 10.2 (broad s, 1H).

Preparation of N-{1-[bis(4-chlorophenyl)methyl]azetidin-3-yl}-N-quinol-6-ylmethylsulfonamide 299.4 g of 1-[bis(4-chlorophenyl)methyl]azetidin-3-ol hydrobromide, 130.8 ml of 10N sodium hydroxide and 3 liters of toluene are placed in a 5-liter reactor equipped with a mechanical stirrer, a thermometer, a 250 ml pressure-equalized dropping funnel and a condenser, and on which is mounted a bubble counter. A suspension is obtained.

The mixture is heated at 50° C. for 1 hour 30 minutes with stirring until a homogeneous two-phase medium is obtained. The phases are separated by settling. The basic aqueous phase is re-extracted with 300 ml of toluene. The organic phases are combined and washed twice with 1138 ml of demineralized water. The toluene phase is distilled in order to remove the traces of water. 730 ml of a toluene/water mixture are distilled off under 155 mbar and at 57° C. 224.2 g of triphenylphosphine and 179.9 g of N-quinolin-6-ylmethanesulfonamide are added in a single portion to the reaction medium at 20±2° C., followed by addition of 700 ml of toluene. An orange-colored suspension is obtained. The reaction medium is heated to 50±2° C.

178.5 ml of diisopropyl azodicarboxylate are added over 1 hour. The reaction is exothermic; the temperature of the reaction medium at the end of addition is 54±2° C. A red solution is obtained. Heating is continued for a further 1 hour 30 minutes at 54±2° C. Heating is stopped and HPLC monitoring is performed to confirm the end of reaction. The mixture is washed twice with 1500 ml of demineralized water. 2330 ml of a toluene/water mixture are distilled off under 173 mbar and at 59±2° C. The distillation is stopped and a further 3 liters of isopropanol are added. The distillation is continued. 2700 ml of a toluene/isopropanol mixture are distilled off under 192 mbar and at 44±2° C. The distillation is stopped and the toluene content in the isopropanol is checked (should not exceed 10% vol/vol). 2600 ml of isopropanol are added with stirring, while maintaining the temperature of the reaction medium at 44° C. Heating is stopped and a crystallization seed is added at 31±2° C. The mixture is allowed to cool to room temperature with slow stirring overnight.

After stirring for 18 hours at 18±2° C., a cream-orange suspension is obtained. The reaction medium is cooled to 13±2° C. for 1 hour and then filtered, and the cake is slurried and then rinsed with 2×381 ml of isopropanol precooled to 10×2° C. The resulting mixture is filtered by suction and dried under vacuum at 35×2° C. to constant weight. 178.1 g of N-{1-[bis(4-chlorophenyl)methyl]azetidin-3-yl}-N-quinol-6-yl-methylsulfonamide are obtained, i.e. a yield of 45%.

$^1$H NMR spectrum (400 MHz)—δ in ppm—in DMSO-d6: 2.76 (m, 2H); 3.02 (s, 3H); 3.42 (m, 2H); 4.40 (s, 1H); 4.85 (m, 1H); 7.31 (broad d, J=8.5 Hz, 4H); 7.36 (broad d, J=8.5 Hz, 4H); 7.59 (dd, J=4.5 and 8.5 Hz, 1H); 7.71 (dd, J=2.5 and 9.0 Hz, 1H); 7.97 (d, J=2.5 Hz, 1H); 8.04 (d, J=9.0 Hz, 1H) 8.39 (dd, J=1.5 and 8.5 Hz, 1H); 8.94 (dd, J=2.0 and 4.5 Hz, 1H).

Preparation of N-{1-[bis(4-chlorophenyl)methyl]azetidin-3-yl}-N-quinol-6-ylmethylsulfonamide dihydrochloride 351.5 g of N-{1-[bis(4-chlorophenyl)methyl]azetidin-3-yl}-N-quinol-6-yl-methylsulfonamide are introduced at 20±2° C. into a 3-liter three-necked round-bottomed flask equipped with a mechanical stirrer, a 500 ml addition funnel and a nitrogen inlet, followed by addition of 1760 ml of methanol. The reaction medium is heated to 50±2° C. 302 ml of a solution of hydrochloric acid in isopropanol (4.9N freshly titrated) are added over 5 min. No exothermicity is observed. A dark yellow solution is obtained after introduction of the solution of hydrochloric acid in isopropanol.

The heating is stopped. A crystallization seed is added at 30±2° C. The mixture is allowed to warm to room temperature over 18 hours. After a contact time of 18 hours at room temperature, a fine beige suspension is obtained.

The reaction medium is cooled to 5±2° C. It is maintained at this temperature for 1 hour. The resulting mixture is filtered through a sinter funnel. The product is washed with 2×350 ml of methanol precooled to 5±2° C. The resulting product is dried in an oven under a vacuum of 10 mmbar at 60° C. to constant weight.

322.9 g of N-{1-[bis(4-chlorophenyl)methyl]azetidin-3-yl}-N-quinol-6-ylmethylsulfonamide dihydrochloride (white crystalline powder) are thus obtained, i.e. a yield of 80%.

Melting point of the N-{1-[bis(4-chlorophenyl)methyl] azetidin-3-yl}-N-quinol-6-ylmethylsulfonamide dihydrochloride: 125° C.

$^1$H NMR spectrum (400 MHz)—δ in ppm—in DMSO-d6 with 75%-25% mixture of conformers: 3.12 (s, 2.2H) and 3.30 (s, 0.8H); from 3.92 to 4.23 (m, 4H); 5.22 (m, 0.7H) and 5.60 (m, 0.3H); 5.99 (broad m, 0.7H) and 6.26 (broad m, 0.3H); 7.47 (broad d, J=8.5 Hz, 4H); 7.72 (broad d, J=8.5 Hz, 4H); from 7.95 to 8.09 (m, 2H); 8.25 (broad s, 0.7H) and 8.38 (broad s, 0.3H); 8.42 (d, J=9.0 Hz, 1H); 8.95 (broad d, J=8.5 Hz, 1H); 9.23 (broad d, J=5.0 Hz, 1H); 13.2 (broad m, 0.3H) and 13.5 (very broad m, 0.7H).

EXAMPLE 2

Preparation of N-{1-[bis(4-chlorophenyl)methyl] azetidin-3-yl}-N-(3,5-difluoro-phenyl)methane-sulfonamide The preparation of the intermediate 1-[bis(4-chloro-phenyl)methyl]azetidin-3-ol hydrobromide is prepared in accordance with the procedures set forth in Example 1

Preparation of N-(3,5-difluorophenyl)methanesulfonamide

The reactor is charged with 14.0 kg of 3,5-difluoroaniline and 56 liters of THF. 9.6 kg of pyridine are added to the stirred solution. The reaction medium is cooled to 0° C. and 13.10 kg of methanesulfonyl chloride are added, while maintaining the temperature between 0-10° C. for 1 hour 30 minutes. At the end of introduction of the methanesulfonyl chloride, the reaction medium is heated at 25° C. for 2 hours. 29 liters of demineralized water and then 6.6 kg of hydrochloric acid (30% w/w) are added to the reaction medium. 60 liters of solvent are distilled off at atmospheric pressure in the presence of an external bath maintained at 100° C., and the reaction medium is then cooled to 20° C. The resulting suspension is filtered and the solid is washed with a total of 20 liters of demineralized water. The solid is dried under vacuum (20 m bar) at 40° C. until a water content <0.5% is obtained. 19.48 kg (87%) of a slightly yellow crystalline solid are thus obtained (m.p.: 121° C.).

N-{1-[Bis(4-chlorophenyl)methyl]azetidin-3-yl}-N-(3,5-difluorophenyl)-methanesulfonamide The reactor is charged with 6.66 kg of 1-[bis(4-chlorophenyl)methyl]azetidin-3-ol hydrobromide, 84 liters of toluene and 28 liters of demineralized water. 3.46 kg of sodium hydroxide solution (30% w/w) are added to this mixture. The reaction medium is stirred for 1 hour at 45° C. and then cooled to 25° C. and, after separation of the phases by settling, the organic phase is recovered and washed three times with 28 liters of demineralized water. The organic phase is added to a reactor charged with 4.87 kg of triphenylphosphine and 3.50 kg of N-(3,5-difluorophenyl)methanesulfonamide. 16 liters of solvent are then distilled off under vacuum with an external bath of 36° C. The reaction medium is heated to 50° C. 3.96 kg of diisopropyl azodicarboxylate (DIAD) are then added over 1 hour and heating is continued for further 1 hour at 50° C. 54 liters of solvent are distilled off under vacuum with an external bath at 55° C., and 100 liters of 2-propanol are then added to the reaction medium, followed by distilling off 60 liters of solvent under atmospheric pressure with an external bath of 90° C. The reaction medium is cooled to 20° C. and stirred at this temperature for 2 hours. The expected product crystallizes in the reaction medium; it is filtered off and the solid is washed twice with 2-propanol (2×10 liters). The solid obtained is placed in a reactor in the presence of 112 liters of 2-propanol, and the reaction medium is refluxed until a clear solution is obtained. The solution is filtered through a filter preheated to 80° C. The expected product crystallizes during cooling to 20° C. Crystallization is continued for 12-24 hours. The product is filtered off and washed three times with 10 liters of 2-propanol. The solid is dried under vacuum (32 and bar) at 50° C.

Yield: 5.72 kg (68%) of a slightly yellow crystalline solid (m.p.: 159° C.).

What is claimed is:

1. A process for the preparation of N-{1-[bis(4-chlorophenyl)methyl]azetidin-3-yl}-N-quinol-6-ylmethylsulfonamide dihydrochloride, which consists of the following steps:
    a) reacting 1-[bis(4-chlorophenyl)methyl]azetidin-3-ol hydrobromide with N-quinolin-6-ylmethanesulfonamide in the presence of diisopropyl azodicarboxylate (DIAD) and triphenylphosphine in toluene at a temperature in the range of from about 40 to about 60° C., to form N-{1-[bis(4-chlorophenyl)methyl]azetidin-3-yl}-N-quinol-6-ylmethylsulfonamide,
    b) removing toluene by azeotropic distillation with isopropanol;
    c) converting the N-{1-[bis(4-chlorophenyl)methyl]azetidin-3-yl}-N-quinol-6-ylmethylsulfonamide dihydrochloride by contacting it with 5-6 N hydrochloric acid; and
    d) crystallizing so formed N-{1-[bis(4-chlorophenyl)methyl]azetidin-3-yl}-N-quinol-6-ylmethylsulfonamide dihydrochloride.

2. The process according to claim 1, wherein step a) is performed at a temperature in the range of from about 45 to about 60° C.

3. The process according to claim 1, wherein step a) is performed at a temperature in the range of from about 50 to about 60° C.

4. The process according to claim 1, wherein step c) is performed in the presence of hydrochloric acid (HCl) in isopropanol.

5. The process according to claim 1, wherein step c) is performed in the presence of isopropanol and 5N hydrochloric acid.

6. The process according to claim 1, wherein step c) is performed in the presence of isopropanol and 6N hydrochloric acid.

7. The process for the preparation of N-{1-[bis(4-chlorophenyl) methyl]azetidin-3-yl}-N-(aryl or heteroaryl)methylsulfonamide, which consists of the following steps:
    a) reacting 1-[bis(4-chlorophenyl)methyl]azetidin-3-ol hydrobromide with N-(aryl or heteroaryl)methanesulfonamide in the presence of diisopropyl azodicarboxylate (DIAD) and triphenylphosphine in toluene at a temperature in the range of from about 40 to about 60° C., to form N-{1-[bis(4-chlorophenyl) methyl]azetidin-3-yl}-N-(aryl or heteroaryl)methylsulfonamide, b) removing toluene by azeotropic distillation with isopropanol; and c) crystallizing so formed N-{1-[bis(4-chlorophenyl)methyl]azetidin-3-yl}-N-(aryl or heteroaryl)methylsulfonamide.

* * * * *